United States Patent [19]

MacLeod et al.

[11] Patent Number: 4,756,707

[45] Date of Patent: Jul. 12, 1988

[54] MOBILE SWIVEL AND TETHER DEVICE FOR ATTACHMENT TO LABORATORY ANIMALS

[75] Inventors: James N. MacLeod, Philadelphia; Bernard H. Shapiro, Melrose Park, both of Pa.

[73] Assignee: Trustees of the University of Pennsylvania, Philadelphia, Pa.

[21] Appl. No.: 69,839

[22] Filed: Jul. 6, 1987

[51] Int. Cl.$^4$ .......................................... A61M 11/00
[52] U.S. Cl. ..................................... 604/93; 119/120; 119/96; 604/261
[58] Field of Search .......................... 604/261; 248/51; 211/162, 113, 94, 13; 119/17, 151, 51 R, 52 B, 120, 96

[56] References Cited

U.S. PATENT DOCUMENTS

| | | | |
|---|---|---|---|
| 1,584,590 | 5/1926 | Archard | 248/51 |
| 1,586,300 | 2/1925 | Fields | 248/51 |
| 1,787,106 | 12/1930 | Glazener | 248/51 |
| 3,043,303 | 7/1962 | Still | 604/66 |
| 3,897,751 | 8/1975 | Gullino et al. | 119/15 |
| 4,690,674 | 9/1987 | Dalglish | 248/51 |

OTHER PUBLICATIONS

V. Popovic, et al., "Permanent Cannulation of Aorta and Vena Cava in Rats and Ground Squirrels", *J. Appl. Physiol.*, 15: 727–728, (1960).
V. Popovic, et al., "Technique of Permanent Cannulation of the Right Ventricle in Rats and Ground Squirrels"; *Proc. Soc. Exptol. Biol. Med.*, vol. 113, pp. 599–602, (1963).
P. Popovic, et al., "Permanent Cannulation of Blood Vessels in Mice"; *J. Appl. Physiol.*, vol. 25, No. 5, pp. 626, 627, (Nov., 1968).
A. Coquelin et al., "Secretion of Luteinizing Hormone in Male Mice: Factors that Influence Release During Sexual Encounter", *Edocrinology*, vol. 106, pp. 1224, 1229, (1980).
"Measurement of Hormones and Blood Gases During Hypoxia in Conscious Cannulated Rats", *J. Appl. Physiol.:* Respirat. Environ. Exercise Physiol., 56 (5), pp. 1426–1430, (1984).
A. K. Chatham, "Jacket and Swivel Tethering Systems", *Lab Animal*, vol. 14 (8), pp. 29–33, (1985).

Primary Examiner—C. Fred Rosenbaum
Assistant Examiner—Colleen M. Reilly
Attorney, Agent, or Firm—Woodcock Washburn Kurtz Mackiewicz & Norris

[57] ABSTRACT

A novel swivel tethering system for attaching to a cage of a laboratory animal is disclosed which provides a greater degree of mobility for laboratory animals. This tethering system provides for extended lateral movement which is not limited to the tether length and is ideally suited for chronic indwelling catheterization since it can minimize the stress created in the animals caused by a limited tether length, thereby reducing the potential distortion of blood parameters.

16 Claims, 1 Drawing Sheet

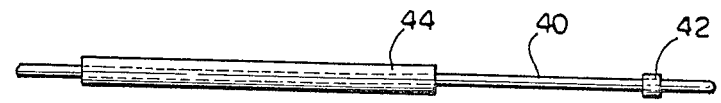
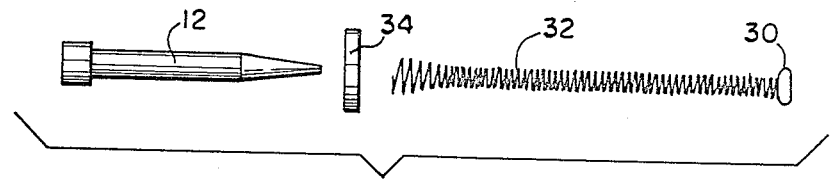
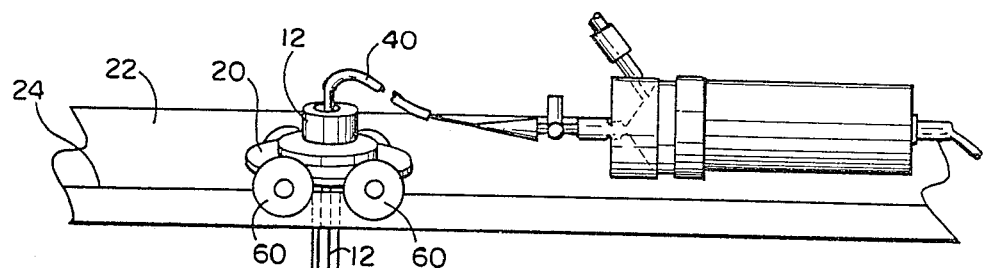
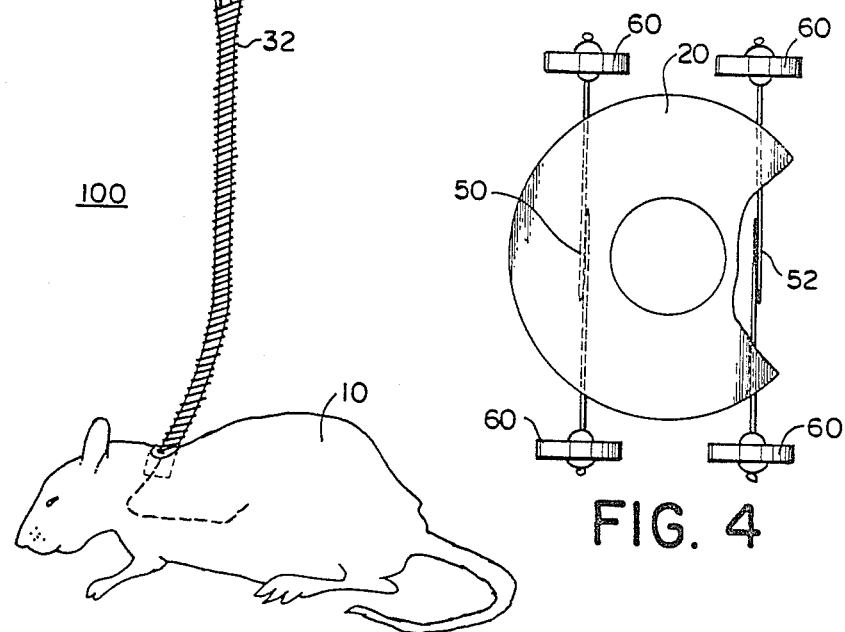

MOBILE SWIVEL AND TETHER DEVICE FOR ATTACHMENT TO LABORATORY ANIMALS

FIELD OF THE INVENTION

This invention relates to apparatus for taking experimental data from unanesthetized laboratory animals, and more particularly, to a swivel tethering system that provide mobility to cannulated, laboratory animals.

BACKGROUND OF THE INVENTION

Traditionally, it was common practice to implant arterial or venous cannulas in larger mammals, such as dogs. These animals were then often used for repeated administrations of predetermined amounts of drugs. More recently, aorta and right ventricle catheterization of rats and ground squirrels has permitted direct measurements of blood pressures and drug absorption without the errors associated with anesthesia and restrainment. V. Popovic et al., *Permanent Cannulation of Aorta and Vena Cava in Rats and Ground Souirrels. J. Appl. Physiol.* 15: 727–728, 1960; V. Popovic et al., *Technicue of Permanent Cannulation of the Right Ventricle in Rats and Ground Squirrels. Proc. Soc. Exptl. Biol. Med.* 113: 599–602, 1963.

Despite these advances, the mouse, a commonly used experimental animal, has been considered too small for permanent catheterization. The small body size of these animals has generally limited blood sampling to nonsurgical methods. With acute terminal procedures, decapitation and trunk blood collection or cardiac puncture are often used. Other situations, however, require multiple sequential blood samples from the same mouse. The easiest and most common techniques involve collection from the caudal blood vessels in the tail. Following immobilization of the mouse, these vessels are either transected, lanced, or punctured to produce hemorrhage. The other common multiple sampling method is retro-orbital membrane puncture and collection from the ophthalmic venous plexus. This is generally considered the preferred nonsurgical approach for repetitive blood sampling in the mouse. However, this approach has drawbacks which include the unavoidable stress of physical or chemical restraint, the potential for excessive trauma and the human psychological discomfort associated with learning and using this technique.

One attempt to provide catheterization to unanesthetized mice is disclosed in P. Popovic et al, *Permanent Cannulation of Blood Vessels in Mice. J. Appl. Physiol.* vol. 25, No. 5, pp. 626, 627 (November, 1968). This article is directed to a technique and apparatus for permanent cannulation for mice using small polyethylene tubings. The cannula of this invention is intended to be disposed in a jugular vein or carotid artery for use in cardiovascular studies or the administration of drugs into the blood stream of the animals. This reference, however, lacks a teaching for a fully mobile catheterization apparatus for reducing stress distortion of blood parameters caused by "leashing" these animals to a limited circular area. While this short length prevents damage from chewing, the mouse must be subjected to the stress of almost full immobilization whenever the catheter is used.

Another mouse cannula is taught by A. Coquelin er al, *Secretion of Luteinizing Hormone in Male Mice: Factors that Influence Release During Sexual Encounters,* Edocrinology, vol. 106, pp. 1224, 1229 (1980). This discussion is direcred to a study for measuring the sequential changes in blood levels of luteinizing hormone during sexual encounters and discloses a chronic cannulation procedure and catheter. The catheter employs a polyethylene stopper which is sutured to the mouse's back. Also included is a swivel means for supporting the entire unit from above and a flare-type tubing adaptor which is soldered to an extension spring that holds the tubing material of the catheter. Although this reference discloses a catheterization apparatus for use in small mammals, such as mice, it also does not disclose a fully mobile device for minimizing stress.

Although, not directed to mouse catheter devices, H. Raffe et al, *Measurement of Hormones and Blood Gases During Hypoxia in Conscious Cannulated Rats,* J. Appl. Physiol.: Respirat. Environ. Exercise Physiol. 56 (5), pp. 1426–1430, 1984, teaches apparatus and methods for implanting chronic arterial cannulas for remote stress-free blood-sampling of conscious unrestrained rats in their own cages. The references discloses the use of lengths of stainless steel spring coils for sheathing the cannulas from the rat to the top of the cage. In addition to these sheaths, the use of quinidine sulfate is disclosed to discourage chewing. The cannula of this reference employs polyethylene tubing of various sizes and subcutaneously implanted stainless steel discs, having a central hollow stem for receiving part of the spring coil. These discs also include a set screw and four suture holes. This reference, however, also fails to disclose a fully mobile in-dwelling catheterization apparatus suited for mice.

Similarly, A. K. Chatham, *Jacket and Swivel and Teathering Systems.* Lab Animal, vol. 14 (8), pp. 29–33, 1985, is directed to restraining devices for larger animals that may include exteriorized catheters and probes for infusing drugs and collecting data. The tethering system consists of a jacket made of a light weight breathable nylon netting material, a light weight, highly flexible stainless steel attaching tether, and a cage-mounted swivel to which the tether is anchored. This reference discloses jacket and swivel tethering systems for use on a variety of research animals, as small as 150 grams, or about five times the weight of an average mouse. As shown in FIG. 3 of this reference, the freedom of movement for the animal is determined by the length of the tether and a fully mobile catheterization apparatus is not disclosed.

Accordingly, there is still a need for a swivel tethering device for use in scientific studies of laboratory animals. There is also a need for a fully mobile catheterization apparatus for obtaining serial blood samples from nonrestrained and unanesthetized mice without the stress associated with confinement to a given tether length.

SUMMARY OF THE INVENTION

A swivel tethering system and catheter are provided for attaching to a cage of a laboratory animal. This tethering system provides for extended lateral movement which is not limited to the tether length. The movement of the laboratory animal is facilitated by a track disposed on the top of the cage and a carriage means attached to the tether and disposed on the track for reciprocal movement along the track. The tethering system is ideally suited for chronic indwelling catheterization apparatus which may be readily disposed coaxially within the tether. Additionally, this invention contemplates that a combination of blood-drawing cannulas and electrical probes could be disposed within the hollow chamber of the tether means.

Thus, a light weight swivel tethering system is provided which overcomes the stress created in the animals caused by a limited tether length, thereby reducing the potential distortion of blood parameters. It has been observed that adult mice can pull the carriage of this invention without apparent effort.

This invention also provides a chronic indwelling catheterization apparatus for the collection of multiple blood samples from mice. Uncontaminated and nonhemolyzed samples can be obtained serially from the same animal at precise time intervals, while simultaneously eliminating potential stress both before and during sample collection. After exiting the mouse, the preferred catheter of this invention can be directed to the outside of the cage to permit nontraumatic collections of multiple uncontaminated blood samples without the necessity of physical or chemical restraint. Since at the time of sampling the cage is preferably not open, behavior of the animal rarely changes and the mouse generally appears unaware that blood collection is occurring. Flexibility of the wire tether, in conjunction with the full longitudinal and rotational mobility of the swivel unit allows a free range of motion to the mouse while simultaneously protecting the catheter from being scratched, bitten, or twisted. Materials used in preparation of the apparatus are readily available and very inexpensive. Pre-surgical assembly of the components of this invention is easy and does not require any specialized equipment. Mobile carts, wire tethers, and cage tops can be used repetitively while new catheters are prepared for each mouse.

In a more preferred embodiment of this invention, a chronic indwelling right atrial catheterization apparatus is disclosed for taking serial blood samples from nonrestrained and unanesthetized mice. This particular system has a light weight carriage means which is generally made from a washer mounted on four wheels. The tether of this embodiment can comprise a pipet tip and washer arrangement that provides for free rotation of the catheter. Also disclosed, is a novel means for attaching the catheter to a mouse which implements a flat perpendicular loop portion of the tether.

It is, therefore, an object of this invention to provide a swivel tethering system that is fully mobile.

It is another object of this invention to provide a swivel tethering system comprising a catheter for obtaining serial blood samples from nonrestrained and unanesthetized mice.

It is still another object of this invention to provide a swivel tethering system that minimizes potential stress distortion of blood parameters.

With these and other objects in view, which will become apparent to one skilled in the art as the description proceeds, this invention resides in the novel construction, combination, arrangement of parts and method substantially as hereinafter described and more particularly defined by the attached claims.

BRIEF DESCRIPTION OF THE DRAWINGS

The accompanying drawings illustrate a complete embodiment of invention according to the best mode so far devised for the practical application of the principles thereof, and in which:

FIG. 1: is a perspective view of a mouse with a complete catheter apparatus attached;

FIG. 2: is a planar view of the catheter illustrating the protective sheath and collar;

FIG. 3: is an exploded, planar view of a preferred tether embodiment illustrating a coiled wire, washer and pipet tip.

FIG. 4: is a top planar view of a preferred carriage means for this invention.

DETAILED DESCRIPTION OF THE INVENTION

In accordance with the teachings of this invention, a swivel tethering system for attaching to a cage of a laboratory animal is disclosed for permitting a laboratory animal to freely move about its cage. The tethering system includes a track disposed on a top surface of the cage and a carriage disposed on the track for reciprocal movement thereon. A tether means is provided which is connected to the animal on one end and attached to the carriage at the other. Included in this tethering means, is a conduit means which may include a catheter for taking serial blood samples or an electrode for monitoring to the laboratory animal.

Referring now to FIGS. 1-3 which illustrate in perspective, planar and exploded views, a swivel tethering system 100 which is the subject of this invention. The swivel tethering system 100 comprises a track 22 disposed of a top surface of an animal cage. Disposed on the track 22 is a carriage means that is capable of reciprocal movement along the track 22. This invention further includes a tether means, shown in the exploded view of FIG. 3, which is rotatably mounted on the carriage means and connected to the animal 10 for tethering the animal 10 to said carriage. Finally, a conduit means is disposed within the tether means for communicating with the animal 10. As FIG. 1 illustrates, the animal, preferably a mouse, may move freely in its cage, carrying the catheter without apparent difficulty. This feature enables experimenters to use larger cages for permitting a greater degree of movement for the test animal, while at the same time maintaining a relatively taunt tether disposed out of the reach of the animal's teeth.

In a preferred embodiment of this invention, the catheter 40 is disposed within said tether means for communicating with said animal 10. Preferably this catheter 40 comprises a protective sheath 44 coaxially disposed around a portion of said catheters' length. The catheter 40 can also comprise a collar 42 disposed near one end of said catheter for serving as a position marker and to stabilize sutures during catheter placement.

The invention further comprises a tether means, as depicted in FIG. 3, including a coiled wise 32 which can comprise a flat perpendicular loop 30 disposed at a bottom portion of said coil 32 for subcutaneous attachment to the laboratory animal 10. The tether means of this invention further can include a washer means 34 for rotatable sliding contact with the carriage means. Further, pursuant to the preferred embodiment of this invention, the tether means can include a pipet tip means 12 disposed within an aperture of the washer means 34 for engaging said catheter 40. Alternatively, the tether means may comprise any swivel means of the type generally known to those skilled in the art.

Also included in a preferred embodiment of this invention, is a novel carriage means which can comprise a wheel for providing reciprocal movement along said track 22. Preferably this carriage means comprises at least two axles 50 and 52 disposed in parallel in a body portion of the carriage means. As designed, these axles preferably include four wheels for providing movement to the carriage means. Accordingly to one preferred embodiment of this invention, the body portion of the carriage means is selected to be a washer 20 having an aperture 54 therethrough. Preferably the axles 50 and 52 in this embodiment are disposed on the washer 20. Finally, accordingly to a most preferred design of this invention, the tether means is removably attached to the carriage means and can be passed into the experimental cage through a slot 24 in the top of the cage.

The catheter 40 of this invention can be made of any biocompatible, flexible tubing, but preferably consists of a 35.0 cm length of SILASTIC tubing by Dow Corning, Midland Mich. Although the length of the tubing can be varied accordingly to the size of the cage and the experimental animal used, a 35.0 cm length has been particularly suitable for use in standard mice cages. The catheter tubing preferably has a inner diameter of about 0.1 to 0.5 mm, more preferably 0.305 mm. The outer diameter of the catheter tubing of this invention preferably has a dimension of about 0.5 to 0.8 mm, and more preferably 0.635 mm.

In a most preferred embodiment of this invention, two segments of polyethylene tubing, obtainable from Clay Adams, Parsippany, N.J., are disposed over the catheter. A 0.2 cm segment of polyethylene tubing, PE-50 from Clay Adams, is positioned about 0.5 to 3.0 cm, preferably 1.5 cm, from the proximal (cardiac) end of the catheter 40. This piece, referred to herein as the "collar" 42, serves as a position marker for the catheter 40 and also stabilizes sutures during catheter placement and surgery. One method of attaching the collar 42 is to slightly enlarge the inner diameter of the collar 42 with a hot water bath and needle forceps to provide easy placement on the silastic catheter 40. It is important for the purposes of this invention, however, that the fit between the collar 42 and the catheter 40 be as snug as possible. In addition to the collar, a second tubing segment, also preferably made of polyethylene, of about 15.0 to 20.0 cm, preferably 18.0 cm in length, is disposed over a portion of the length of the catheter 40. Preferably this second tubing is made from size PE-60 polyethylene tubing from Clay Adams. This segment, referred herein as the "protective sheath", protects the portion of the catheter 40 not beneath the skin surface of the animal 10. Finally, the catheter lumen dead space of this invention is approximately 30 μl.

The tether means of this invention is designed for two distinct functions. First, it directs the exposed portion of the catheter 40 up through the cage top. Second, it protects the catheter from manipulation or destruction by the mouse. The tether means of this invention is preferably made of using 26 gauge stainless steel wire, a metal washer (of about 5/16" inner diameter and ⅜" outer diameter), and a 1.0 ml polyproplylene pipet tip, as substantially described in FIG. 3. The length of the tether means depends ultimately upon the depth of the cage and the size of the experimental animal. The tether must comfortably extend from the dorsum of the experimental animal, preferably a mouse, to the carriage on the top of the cage. The stainless steel wire is preferably tightly coiled along most of its length with an inner diameter of approximately 1.5 mm. Since the protective sheath 44 preferably has an outer diameter of 1.22 mm, it will fit comfortably within the coiled wire 32. Additionally, the top of the coiled wire 32 is made progressively wider in order to facilitate attachment to the polyproplylene pipet tip 12. In this preferred design, the top 1.5 cm of the coiled wire 32 is expanded in a funnel shape, accordingly to FIG. 3. It is desired that the exposed coils be very close together in order to deny the mouse any access to the catheter 40. The metal washer 34 is designed to be pushed as far as possible onto the pipet tip 12 which is then attached to the wire coil 32, preferably with ZONAS porous tape from Johnson & Johnson Co., New Brunswick, N.J. Finally, the bottom portion of the coiled wire 32 can be formed into a flat perpendicular loop 30 for subcutaneous attachment to the laboratory animal 10.

The preferred carriage means of this invention has the basic design of a miniature cart which includes a metal washer "body", straight pin "axles", and sew-on snap "wheels", as depicted in FIG. 4. Preferably, one size 3, sew-on snap wheel from Dritz Inc. is placed on each of the four straight pins. Two pins are then taped together to produce an "axle" 50 and 52. By gluing a front and a back axle to the metal washer 20, preferably having dimensions of about 7/16" inner diameter and about 1.0" outer diameter, the carriage means is created. It is important to this embodiment that each wheel 60 spins freely and that the front axle be disposed in parallel to the back axle so that the carriage means rolls in a straight line.

The carriage means of this preferred embodiment is designed to support the coiled wire 32 which passes into the cage, preferably through about a 1.2 cm wide median slot in an opaque plastic cage top. Thus, the catheter 40 can pass up away from the mouse and out the top of the cage completely protected within the tether. Blood samples then can be collected without even opening the cage. Experimental and direct observations indicate that catheterized mice are unaware of any changes even during the actual sampling process. Longitudinal mobility of the catheter apparatus results as the mobile cart rolls along the cage top on track 24. Rotational mobility is achieved because the tether is supported by but not attached to the carriage means of the preferred embodiment. Again, it has been observed that adult mice can pull the cart and have freedom of movement without apparent effort.

Although surgical methods of catheter placement are known, the following preferred procedure proved useful with respect to this mobile system of this invention. Pentobarbital was initially used as the anesthetic agent. An induction dose of 80 mg/kg body weight (2.4 mg for a 30 g mouse) was then administered intraperitoneally (i.p.) to produce general anesthesia within 5 minutes. Additional 20 mg/kg i.p. doses were then given during the procedure as needed to maintain unconsciousness. The nails on all hind leg digits were clipped after induction of anesthesia. This practice largely eliminates mouse-inflicted damage to the catheter or suture lines during the period of post-surgical adaptation to the catheter apparatus. Two surgical sites, the right ventral neck and chest region and dorsally between the shoulders, were next prepared by shaving the hair and aseptically washing both regions with a dilute mild soap and 70% ethyl alcohol. A stereomicroscope was also used during surgery. The right external jugular vein was then approached through a 1.0 cm ventral paramedian skin incision and isolated by careful blunt dissection. The vessel wall is very easy to tear and should never be grasped directly. Two 5-0 silk ligatures were then placed at least 0.2 cm apart, both distal to the origin of the axillary vein. The rostral ligature was then tightened and a small cut was made in the ventral aspect of the external jugular vein between the two ligatures with iris scissors. The silastic catheter, filled with a heparinized saline solution (10 I.U./ml)and attached to a microsyringe was then gently inserted into the vessel. Difficulty in advancing the catheter may be experienced at the level of the thoracic inlet. In this event, it is preferred that the catheter be withdrawn and rotated slightly prior to further advancement.

Once the catheter enters the right atria, the beating of the heart against the catheter's proximal end will be readily apparent. The catheter can then be withdrawn about 2.0 mm to properly position the proximal end just inside the right atria (the beating of the heart should no longer be felt). Patency of the lumen can be checked by drawing back on the microsyringe and watching for a free flow of blood. The catheter can be secured by tightening the proximal ligature and tying additional knots around the PE-50 collar. After exiting the jugular vein, the catheter can be directed subcutaneously along the side of the neck and passed out through a dorsal skin incision between the shoulders. The ventral incision can then be closed.

In a preferred design, an opaque plastic cage top, mobile carriage unit, and wire tether, all supported by a ring stand are positioned over the mouse. The catheter 40 can be passed up through the coiled wire 32 and exited through the tether on the outside of the cage top. The tether an be attached to the mouse by closing the dorsal incision around the perpendicular loop at the base of the coils. The PE-60 tubing sheath preferably can extend the entire length of the tether in order to protect the silastic catheter within. Following surgery, the mouse, catheter, tether, and cage top become a single unit and can be moved together. The open end of the silastic catheter preferably is occluded with a 1.5 cm 27 gauge metal brad.

Right atrial catheters of this invention have been successfully placed in mice. Post-surgically, mice have adapted quickly to the presence of the catheter apparatus, and within several hours, behavior patterns have appeared normal. The period of catheter patency has been observed to vary from 10 days to 2 months and can be improved as surgical and catheter management experience is accumulated. On the average, however, experimental use of the preferred catheters of this invention indicated that these devices remained fully patent for 21.5 days allowing more than 4.0 ml of blood to be obtained per mouse. The experimental collection schedule, 250 μl of blood collected for 3 successive days followed by 1 day of rest, resulted in a temporary red blood cell anemia. The average hematocrit dropped by to 31% by day 3, but returned to normal limits by day 5. Peripheral reticulocytes, counted to monitor the hematopoietic response, rose to a corrected value of 14% by day 6 and stabilized at approximately 7% by day 11. Moreover, total plasma protein values did not change significantly. Corticosterone concentrations in blood samples obtained from catheterized mice were similar to levels in rapidly killed nonstressed controls. However, stress in the form of physical handling for a duration of 15 minutes prior to trunk blood collection markedly elevated plasma corticosterone concentrations in both sexes, with a greater response in females.

From the foregoing, it can be realized that this invention provides an improved swivel tethering system for attaching to a cage of a laboratory animal. Specifically a fully mobile chronic indwelling right atrial catheterization apparatus has been disclosed in order to obtain serial blood samples from nonrestrained and unanesthetized mice. The system is unique in that, despite the small size of the mice, multiple, uncontaminated blood samples can be obtained over extended periods of time while the animals remain completely undisturbed. Potential stress distortion of blood parameters due to handling, restraint and leashing the animal to a limited circular area, therefore, is effectively eliminated. The apparatus has special application to blood clearance studies and for the determination of changes in the blood concentration of endogenous compounds over time. As disclosed, the preferred catheter apparatus comprises three parts: the catheter, a stainless steel wire tether means, and a carriage means. Each of these parts can be prepared beforehand and easily assembled during surgical placement of the preferred catheter in a mouse. Although various embodiments have been illustrated, this was for the purpose of describing, but not limiting the invention. Various modifications, which will become apparent to one skilled in the art, are within the scope of this invention described in the attached claims.

We claim:

1. A swivel tethering system for attaching to a cage of a laboratory animal, comprising:
   (a) a track disposed on a top surface of said cage;
   (b) a carriage means disposed on said track or reciprocal movement along said track;
   (c) a tether means rotatably mounted on said carriage and connected to said animal for tethering said animal to said carriage; and
   (d) conduit means disposed within said tether means for communicating with said animal.

2. The system of claim 1 wherein said conduit means comprise a catheter.

3. The system of claim 1 wherein said conduit means comprises an electrode.

4. The system of claim 2 wherein said catheter comprises a protective sheath coaxially disposed around a portion of said catheter's length.

5. The system of claim 4 wherein said catheter further comprises a collar disposed near one end of said catheter.

6. The system of claim 1 wherein said tether means comprises a coiled wire.

7. The system of claim 1 wherein said tether means further includes a washer means for rotatable sliding contact with said carriage means.

8. The system of claim 7 wherein said tether means further includes a pipet tip means disposed within an aperture of said washer means for engaging said catheter.

9. The system of claim 1 wherein said tether means comprises a swivel.

10. The system of claim 9 wherein said carriage means comprises a wheel for providing reciprocal movement along said track.

11. The system of claim 1 wherein said carriage means comprises at least two axles disposed in parallel on a body portion of said carriage means, said carriage means having at least four wheels attached to said axles.

12. The system of claim 11 wherein said body portion comprises a washer.

13. The system of claim 12 wherein said axles are disposed on said washer.

14. The system of claim 1 wherein said tether means is removably attached to said carriage means.

15. The system of claim 14 wherein said tether means is passed into said cage through a slot in the top of said cage.

16. The system of claim 6 wherein said coiled wire comprises a flat perpendicular loop disposed at a bottom portion of said coil for subcutaneous attachment to said laboratory animal.

* * * * *